Figure 1:
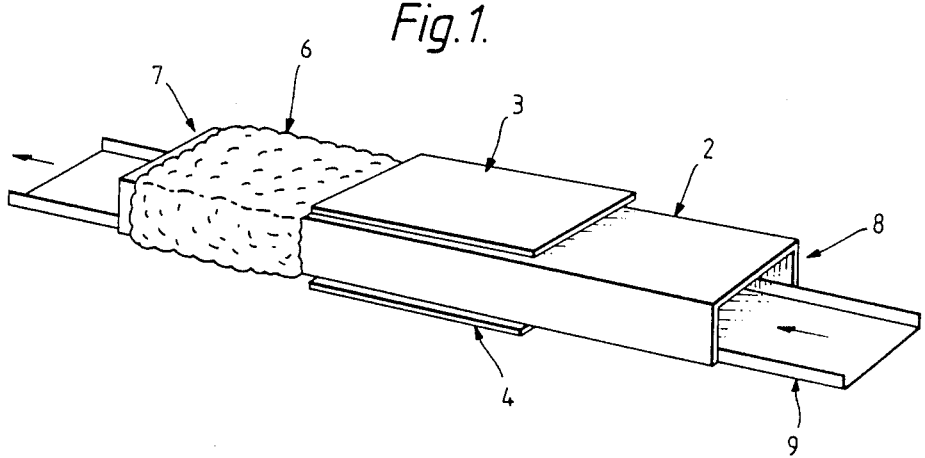

United States Patent [19]

Diprose et al.

[11] Patent Number: 4,978,501
[45] Date of Patent: Dec. 18, 1990

[54] CONTINUOUS PROCESS FOR THE PARTIAL STERILIZATION OF MUSHROOM CASING

[75] Inventors: Michael F. Diprose, Derbyshire; Geoffrey H. Evans, Hartford, both of England

[73] Assignee: Minister of Agriculture, Fisheries & Food, etc., London, England

[21] Appl. No.: 287,654

[22] Filed: Dec. 21, 1988

Related U.S. Application Data

[63] Continuation of Ser. No. 38,070, Apr. 14, 1987, abandoned.

[51] Int. Cl.⁵ ............................ A61L 2/08; B01J 19/02
[52] U.S. Cl. ..................................... 422/22; 219/388; 422/186.04; 422/186.29
[58] Field of Search .............. 422/22, 186.29, 186.01, 422/32, 23, 186.04–186.06, 186.2; 219/388

[56] References Cited

U.S. PATENT DOCUMENTS

| | | | |
|---|---|---|---|
| 3,092,503 | 6/1963 | Gray | 422/22 |
| 3,233,030 | 2/1966 | Connell et al. | 422/186.29 X |
| 3,341,280 | 9/1967 | Eolkin | 422/32 X |
| 3,494,724 | 2/1990 | Gray | 422/22 |
| 4,207,286 | 6/1980 | Boucher | 422/22 |
| 4,252,595 | 2/1981 | Yamamoto et al. | 422/186.05 X |
| 4,309,388 | 1/1982 | Tenney et al. | 422/30 X |

FOREIGN PATENT DOCUMENTS 0104868 9/1938 Australia ............................ 422/22

Primary Examiner—Robert J. Warden
Assistant Examiner—Amalia Santiago
Attorney, Agent, or Firm—Nixon & Vanderhye

[57] ABSTRACT

A process and apparatus are provided for the sterilization of horticultural material, which may be substrate, fertilizer, peat or especially mushroom casing. The sterilization may be complete or may be partial, removing only harmful organisms while leaving beneficial organisms unharmed. The horticultural material is passed through a tunnel and is exposed to radiofrequency electromagnetic waves for a period sufficient for sterilization. In a preferred process and apparatus the horticultural material is heated to a suitable temperature by the waves and is then maintained in a region not exposed to the waves for a period long enough to sterilize the material, before allowing it to cool to ambient temperature.

15 Claims, 2 Drawing Sheets

CONTINUOUS PROCESS FOR THE PARTIAL STERILIZATION OF MUSHROOM CASING

This is a continuation of application Ser. No. 07/038,070, filed Apr. 14, 1987, now abandoned.

The present invention relates to a continuous process for the sterilization of horticultural materials in particular for the partial sterilisation of mushroom casing, and to an apparatus for carrying out the process.

It is frequently necessary in horticulture to sterilize horticultural materials, e.g. substrates such as soils, peat, rockwool fiber etc. or fertilizers to remove harmful organisms such as flies, fungi and mites. In some cases however it is desirable to only partially sterilize the material, so as to remove harmful organisms without killing beneficial organisms, particularly certain bacteria. This is especially so in mushroom production, where partial sterilization of mushroom 'casing' is carried out.

The production of mushrooms has three distinct phases. In the first, the cultivation step, pure culture spawn is introduced into prepared beds of mushroom compost. For good growth of the mushroom mycelium throughout the compost, the culture spawn should be broken into small pieces and, when the temperature of the compost is about 30° C., pressed into the beds about 25 cm apart. The growth of mycelium through the compost is described as a 'run'. This period usually lasts from 15 to 30 days, during which time conditions of temperature, humidity and ventilation are kept at an optimum, while pests infecting the compost are kept to a minimum.

The next stage in the process is the casing step. Once the mycelium has penetrated throughout the compost, the bed is moistened and a thin layer of mushroom casing is spread over the surface. This is done for a number of reasons:

(a) Mushrooms form on the surface of the compost, but they are heavy, and if there is nothing to support them they may fall over and break the 'roots' through which it derives sustenance.

(b) The surface of the compost dries out very readily, and it is extremly difficult to replace the evaporated water without killing the spawn. The casing layer prevents drying out.

(c) Vegetative mycelium is encouraged to fruit when it enters a medium deficient in food, it attempts to ensure its survival by producing fruit containing spores. A suitable casing material provides this medium.

An ideal casing material is one which has the following characteristics:

(a) It absorbs water quickly and releases it slowly.

(b) Its water holding capacity is such that it can be watered without sealing off the compost.

(c) Its texture is not substantially altered by watering.

(d) It is neither acid nor alkaline, but neutral.

(e) It must contain a bacterial flora which promotes fruiting.

(e) It is free from disease organisms and insects.

(f) It is free from undecomposed vegetable matter (which is susceptible to attack by undesirable molds).

The most commonly used casing material is a mixture of peat and chalk or lime, but other materials which have been used or contemplated are peat alone (if neutral) weathered mushroom compost, recycled paper pulp, recycled sugar beet lime, and some soils. Research continues to find other materials.

About 5 weeks after casing, the first 'flush' of mushrooms are ready for collection and the final stage of cropping and packing.

During the entire cultivation process the presence of fungi and invertebrate pests, such as flies, mites and nematodes must be minimized. For mushroom casing, the control of these pests and fungi has traditionally been achieved by steam treatment of the casing prior to use. However there are a number of disadvantages associated with the use of steam. First the capital cost is high. Second, uniformity of treatment is practically impossible since a temperature differential in the casing will occur. Thirdly a wide variation in sample temperature occuring when steam is used will mean that some bacteria which are beneficial to mushroom growing, as well as pests will be destroyed.

There has been some discussion of the possibility of the use of radiofrequency radiation to destroy microorganisms in soils, but there is considerable uncertainty as to the mechanism of destruction, and to the optimum conditions for destruction. For example Baker and Fuller, Phytopathology, 59, 193–197 (1969) conclude that the efficiency of destruction is very dependent on soil moisture content, whereas Ferris, American Phytopathological Society, 74, 121–126, (1984) concludes that soil moisture content has no effect. While the experiments described in these publications have been carried out on soils, no suggestion has ever been made as to the effect of radiofrequency radiation on the novel medium of mushroom casing.

It is one object of the present invention to provide a process for the sterilization of horticultural materials (as described above) and especially for the partial sterilization of mushroom casing.

It is a further object to provide sterilization apparatus to carry out that process.

According to one aspect of the present invention there is provided a continuous process for the sterilization of horticultural material comprising continuously passing wet horticultural material through a tunnel and exposing at least a part of the material within the tunnel to radiofrequency electromagnetic waves, the length of exposure to the waves being such that fungi and invertebrate pests are destroyed.

In a preferred form of the process, more suited to but not exclusively for the partial sterilization of horticultural material and especially for mushroom casing, the wet material or wet casing is continuously passed through a tunnel and at least part of the material or casing is exposed to radiofrequency electromagnetic waves, length of exposure to the waves being such as to heat the material or casing to a temperature which will sterilize the material or casing, and subsequent to the exposure maintaining the material or casing substantially at that temperature for $\propto$ predetermined time in a region not exposed to the waves, before allowing the material or casing to cool to ambient temperature.

Sterilization in this latter form of the process may be partial or complete depending upon the combination of temperature and time. A suitable temperature for both is 90°–100° C. The time for which the temperature is maintained may be between 30 seconds and 20 minutes. The latter time is generally sufficient for complete sterilisation at the quoted temperatures, and for partial sterilization of mushroom casing a time of around 2 minutes is generally sufficient.

According to a second aspect of the invention, there is provided a sterilizes for horticultural material (as defined above) adapted for continuous operation comprising a set of radiofrequency electromagnetic wave applicators and between the applicators a tunnel which at least between the applicators is of a low loss dielectric material, the tunnel being adapted for passage of material therethrough and also adapted to exclude water vapor emanating from the tunnel, from the applicators.

In a preferred form of the sterilizer, the tunnel extends downstream beyond the applicators and in the extended region at least is adapted to substantially maintain the temperature of heated material contained therein for a predetermined time.

The sterilizer facilitates the performance of the process of the invention and the preferred form of the sterilizer is particularly intended for the preferred form of the process and for partial sterilization.

The radiofrequency electromagnetic waves may be microwaves but are preferably radiofrequency waves of frequency 13 to 100 MHz. The use of such waves for the sterilization of horticultural materials has a number of advantages over the use of steam. Firstly, all parts of the exposed material are treated simultaneously and thus at the same rate, enabling uniform treatment.

Secondly radiofrequencies are cheap to produce, the equipment necessary being simple and commercially available. A number of rf frequencies are allocated by national laws to food industry use, and of these 27.12 MHz is preferred.

Thirdly, and as a consequence of the uniform treatment, the process is easily controllable to achieve conditions suitable for partial sterilization.

A particular advantage of the preferred process and sterilizer of the invention is their energy efficiency. By maintaining the temperature of the material without the need for further exposure to waves, the power input may be dedicated solely to initially raising the temperature to the desired range, without energy waste in simply boiling off water. The parameters of electrical power, dimensions of the tunnel flow rate of the material etc. discussed below have been devised by the inventors to optimize energy efficiency and hence running costs.

Heating by rf electromagnetic waves relies upon non-conducting materials absorbing waves passing through them and converting the energy absorbed into heat. The amount of energy absorbed is given by the following equation:

$$P_{abs} = 2\pi f \epsilon_o \epsilon_r \tan\sigma E^2 \text{ Watts } m^{-3}$$

where
f = frequency (Hz)
E = electric field strength (Vm$^{-1}$)
$\epsilon_o = 8.854 \times 10^{-12}$ (Fm$^{-1}$)
$\epsilon_r$ = relative dielectric constant
tan $\sigma$ the loss tangent The factors $\epsilon_r$ and tan $\sigma$ depend upon the material, its temperature and usually vary with frequency. It can be seen that the higher $\epsilon_r$ and tan $\sigma$ are the greater the energy absorbed for particular values of f and E. For this reason materials such as mushroom casing must be wet for rf heating as its tan $\sigma$ value is very low when dry.

The process and sterilizes of the invention have been found to be suitable for use with horticultural materials with a wide range of water contents, and water contents from 20 up to 200 wt. % have been successfully sterilized. An optimum water content for mushroom casing partial sterilization is 100 wt. %, i.e a 1:1 wt. ratio of dry casing to contained water. The sterilized output may of course have its water content adjusted to a useful level, e.g. by addition of extra water.

It is desirable that the period of exposure of the wet horticultural material to the rf waves is just sufficient to heat the material to 90°–100° C. If the period is longer, then energy is wasted in simply boiling off water without any further rise in temperature. Furthermore, if this water evaporates, the material will dry out and the efficiency of heating will decrease, so the temperature may drop. It has been found to be beneficial however to reach the temperature of 90°–100° C. about 85% of the way through the heating period in some applications.

Using a commercially available 20 KW rf generator suitable heating may be achieved in a layer of wet horticultural material of maximum thickness 10 cm, a preferred thickness being 7.5–10 cm. The air gap between the applicators and the material should be the minimum possible to avoid power loss without causing arcing. A power density of up to 60 KW m$^{-2}$ is preferred, with a maximum of 90 KW m$^{-2}$, for such a thickness. A period of exposure to the rf waves of around 1–2 minutes under these conditions is generally adequate for the heating to 90°–100° C., but the precise conditions may be determined by experiment. These exposure conditions may be achieved by a suitable combination of flow speeds and length and width of the exposure region.

The choice of rf wave generator and applicators will be entirely conventional. Generators of 20 and 50 KW output are available commercially. The use of a larger generator and larger dimensions of tunnel may increase throughput of material but it is generally more convenient to use a number of sterilizers of lower capacity in parallel, so that if the generator breaks, the process need not be halted completely. It is generally advisable and is often a legal requirement that the generator and applicators are shielded to avoid exposure of workers to radiation. The amount and type of shielding will be governed by local laws.

The applicators may for example be a number of bars or plates surrounding the tunnel. In a preferred embodiment the rf applicators consist of two parallel plates of metal e.g. copper placed on opposite sides of the tunnel.

The tunnel may be of any convenient cross sectional shape, but a preferred shape is rectangular. The tunnel should be steam-tight to retain water within the horticultural material and to prevent steam contacting the applicators.

The tunnel in the region of the applicators should be constructed from any low loss dielectric material, that is any material with a low dielectric constant. Typical of such materials, which are essentially transparent to rf waves are sodaborosilicate glass, certain polymers such as PTFE, polyethylene, polystyrene, polypropylene, certain ceramics and silicon resin bonded fiberglass.

The extended region of the tunnel where the horticultural material is not exposed to rf waves may be of any convenient material, and may be integral with the tunnel region between the applicators and so made of the same material. If the two regions are not integral the join should be steam-tight. The extended region should either have good insulating properties or be covered with an insulating material to retain the temperature, although a temperature drop of 10°–15° C. may be acceptable in some applications. The extended region of the tunnel, if not integral may for example be of insulated aluminum.

The length of the extended region is determined only by practical limits, but a minimum of about 0.5 m has been found desirable to avoid contact of the applicators by steam. Determination of a suitable length to achieve a desired sterilization time as discussed above for a given flow rate and cross section may be determined by the method for detecting harmful organisms described below.

It is also desirable to extend the tunnel upstream of the applicators so that steam given off as the wet horticultural material is heated may preheat the incoming material, further reducing energy waste. An upstream extension of 0.5-1.0 m has been found adequate in a tunnel of cross section $30 \times 10$ cm.

It should be noted that unlike the steam sterilizations of the prior art, the degree of heating by the steam generated in the present process and sterilizer is not sufficient to kill bacteria present in mushroom casing.

In the present process and sterilizer, horticultural material is passed contiuously through the tunnel. This may be achieved for example by a conveyor belt or an archimedean screw passing along the tunnel. These should be made of low dielectric constant materials to avoid heating. Alternatively the tunnel may be placed at an angle to the ground and the material passed through the tunnel by the pull of gravity, optionally encouraged by agitators. It is desirable that the tunnel is substantially filled by the horticultural material to avoid air spaces in the tunnel. Other methods of passing the material through the tunnel will be apparent to those skilled in the art.

The speed at which the horticultural material is passed through the tunnel will be determined in particular by the size of the tunnel, the shape of the tunnel, the power input, water content etc. Using a rectangular tunnel 30 cm $\times$ 10 cm deep, a 20 KW rf generator, two rectangular applicators 2 m $\times$ 30 cm a conveyor belt speed of 1 m min$^{-1}$ was found to be entirely adequate.

After the horticultural material has passed through the process of the invention it is desirable to cool it as quickly as possible, e.g. by water spraying of the downstream end of the tunnel so as to avoid destruction of beneficial organisms in a partial sterilization process, and to permit early handling.

The presence of harmful fungi and pests may be detected in the processed horticultural material, in the case of pests by visual inspection, or in the case of fungi by germination followed by visual inspection. Other methods of detection will be known to those skilled in the art. In the case of mushroom casing, the presence of pests or fungi may be detected simply by use in the cultivation of mushrooms, when symptoms of infestation will be quickly manifested if pests or fungi are present. Such symptoms are widely recorded, see for example Mushroom Growing Today, 5th edn., 1966, chapters 17 and 20.

Figure 2:
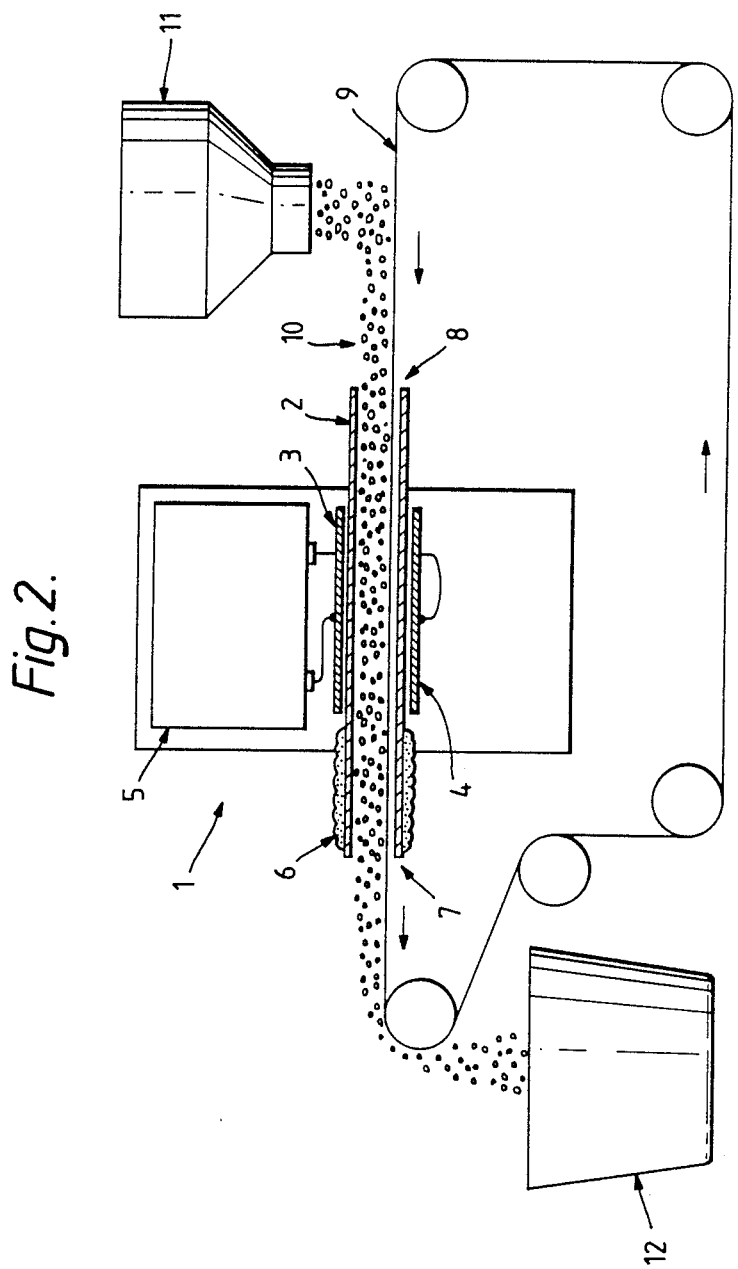

The invention will now be described by way of example only with particular reference to FIGS. 1 and 2 in which:

FIG. 1 Shows a schematic perspective view of a tunnel and applicators according to the invention, and FIG. 2 Shows the tunnel and applicators in position in a sterilizer.

Referring to the Figures a mushroom casing partial sterilizer is shown generally at (1). A glass tunnel (2) of rectangular cross section $30 \times 10$ cm passes between two parallel rectangular copper applicator plates (3,4). These plates (3,4) are positioned above and below the central portion of the tunnel (2). The tunnel (2) and applicators (3,4) are within the shielded body of a commercially available 20 KW, 27 MHz rf generator (5) supplied by Induction Heating Equipment Ltd, Horsham, Sussex, UK, and the applicators (3,4) are connected to the output of the generator (5) by copper strip connectors. A region (6) of the tunnel (2) is covered with a thermal insulating material, glass wool, and the two ends (7,8) of the tunnel (2) project outside the body of the rf generator (5). A conveyor belt (9) passes through the tunnel (2). The insulated region (6) is downstream and about 2 m long. The upstream end (8) is about 1 m long.

In use, mushroom casing (10) from a feed hopper (11) is passed onto the conveyor belt (9). A tensioner (not shown) was found to be necessary to compensate for expansion of the belt (9). A belt speed of 1 m s$^{-1}$ was used. Casing on the belt (9) enters the tunnel (2) and is then irradiated with rf waves at 27.12 MHz passing through the tunnel from the applicators (3,4). It was found to be necessary to 'tune' the position of the applicators (3,4) to achieve maximum absorption of rf waves by the casing (10), as measured as a maximum anode current reading, by raising and lowering the upper applicator (3) using an electric servo motor (not shown). This tuning was easily automated.

During the process steam is generated within the tunnel (2) and moves in both directions along the tunnel (2). In the upstream direction the steam preheats casing moving towards the rf field, while in the downstream direction the steam maintains the treated casing at a high temperature, the bulk of the temperature loss being reduced by the insulator (6).

The treated casing, in which both pests and fungi have been destroyed but beneficial bacteria are unharmed passes out of the end (7) of the tunnel (2) and is deposited into the collection vessel (12).

RESULTS

A trial was performed to illustrate the growth of mushrooms on three casing mixtures, (a) An uncontaminated, untreated peat/chalk mixture.

(b) An untreated peat/chalk mixture contaminated with *Verticillium fungicola.*

(c) A peat/chalk mixture initially contaminated with *Verticillium fungicola* as in (b) but exposed to rf treatment in the manner described herein prior to use.
Results were as follows:

(a) The mushrooms produced showed no visible differences from the commercial yield.

(b) Very few mushrooms of acceptable quality were produced due to dry bubble disease caused by *Verticillium fungicola*. 95% of the mushrooms were infected with this disease.

(c) The mushrooms produced showed no visible differences from the commercial yield and no sign of disease. Colonization of the casing layer took place more quickly using this treated casing than when the untreated uncontaminated casing was used and the yield obtained was in some cases greater by about 20% than that obtained using uncontaminated untreated casing. Typical yields were 16 kg m$^{-2}$.

We claim:

1. Apparatus for at least partially sterilizing wet horticultural material comprising:

an open ended tunnel having a channel extending therethrough, said tunnel defined by steam tight walls, constructed of low loss dielectric material in at least a central portion of said tunnel;

radio frequency wave electromagnetic applicator means positioned at least on opposite sides of said central portion of said tunnel for heating wet horticultural material passing through said tunnel to a predetermined temperature in the range of about 90°-100° C., said tunnel having no other heat generating means associated therewith, and wherein said radio frequency wave applicator means is capable of emitting RF radiation at a frequency of 13 to 100 MHz, and of applying an RF power density of up to 90 KW m$^{-2}$;

means for continuously passing the wet horticultural material through said tunnel at a speed such that the material is exposed to the heating effect of the radio frequency waves when applied by the applicators for a period of 1-2 minutes, said tunnel being provided with a first extended region immediately adjacent and upstream of said radio frequency wave applicator means adapted to expose incoming material when in the said first extended region to steam given off from the heated material, and said tunnel being provided with a second extended region immediately adjacent and downstream of said radio frequency applicator means and wherein the said downstream extended region includes insulation means for maintaining the wet horticultural material at substantially said predetermined temperature and exposes outgoing material to steam given off from said heated material.

2. A sterilizer according to claim 1 wherein said first extended region has a length of about 0.5 to 1.0 meter.

3. A sterilizer according to claim 1 wherein said second extended region has a length of at least about 0.5 meter.

4. A sterilizer according to claim 1 wherein the said means to continuously pass material through said tunnel comprise a conveyor belt passing through and along the length of the tunnel.

5. Apparatus according to claim 1 wherein said radio frequency wave applicator means is capable of applying an RF power density of up to 60 KWm$^{-2}$.

6. Apparatus according to claim 1 wherein said radio frequency wave applicator means comprises a pair of parallel radiating plates.

7. Apparatus according to claim 1 wherein said tunnel is substantially rectangular in shape with a cross-sectional dimension of about 30×10 cm$^2$.

8. Apparatus according to claim 1 wherein said radio frequency wave applicator means comprises a 20 KW, 27 MHz generator.

9. A process for at least partially sterilizing wet horticultural material comprising the steps of:
(a) providing an open ended tunnel having radio frequency wave applicator means positioned at least above and below a central portion of the tunnel, said tunnel being defined by steam tight walls constructed of low loss dielectric material in at least a central portion of said tunnel;
(b) continuously passing wet horticultural material through said tunnel; and
(c) exposing at least a part of said wet horticultural material to radio frequency waves in a frequency range of 13 to 100 MHz and at a power density of up to 90 KWm$^{-2}$ for a period of 1-2 minutes to heat said material to a predetermined temperature of 90°-100° C., and thereafter to the heat generated by said waves for a period of time in the range of about 30 seconds to about 20 minutes sufficient to destroy fungi and invertebrate pests, and further wherein as a result of heating said wet horticultural temperature to said predetermined temperature, steam is generated; the process including the further step of:
(d) utilizing said steam upstream of said radio frequency wave applicator means to preheat the wet horticultural material, and downstream of said radio frequency wave applicator means to maintain the wet horticultural material at a temperature within about 10° to 15° C. of said predetermined temperature without utilization of additional heating means.

10. A process according to claim 9 wherein said horticultural material comprises fertilizer.

11. A process according to claim 9 wherein said horticultural material comprises peat.

12. A process according to claim 9 wherein said horticultural material comprises mushroom casings.

13. A process according to claim 9 and including the further step of cooling said wet horticultural material immediately after step (d).

14. A process for partially sterilizing wet mushroom casing material comprising the steps of:
(a) providing an open ended tunnel having radio frequency wave applicator means positioned at least above and below a central portion of the tunnel, said tunnel being defined by steam tight walls constructed of low loss dielectric material in at least a central portion of said tunnel;
(b) continuously passing wet mushroom casing material through said tunnel; and
(c) exposing at least a part of said wet mushroom casing material to radio frequency waves in a frequency range of 13 to 100 MHz for a period of 1-2 minutes to heat said material to a temperature of 90° to 100° C., and thereafter to the heat generated by said waves for a period of time in the range of about 30 seconds to about 20 minutes sufficient to destroy fungi and invertebrate pests and wherein as a result of heating said wet mushroom casing to said predetermined temperature, steam is generated; the process including the further step of:
(d) utilizing said steam upstream of said radio frequency wave applicator means to preheat the wet mushroom casing and downstream of said radio frequency wave applicator means to maintain the wet mushroom casing at a temperature within about 10° to 15° C. of said predetermined temperature without utilization of additional heating means.

15. A process according to claim 14 and including the further step of cooling said mushroom casing immediately after step (d).

* * * * *